United States Patent [19]

Mündel

[11] 4,147,907
[45] Apr. 3, 1979

[54] GAS LEAKAGE INDICATION DEVICE
[75] Inventor: Erwin Mündel, Linköping, Sweden
[73] Assignee: Leif Tage Petersen, Sweden
[21] Appl. No.: 782,584
[22] Filed: Mar. 29, 1977
[30] Foreign Application Priority Data
Mar. 31, 1976 [SE] Sweden .......................... 76038405
[51] Int. Cl.² ...................... G01N 27/12; H01H 35/00
[52] U.S. Cl. .................................. 200/61.03; 340/633; 422/98
[58] Field of Search ................ 116/114 P; 23/230 L, 23/255 E; 137/551; 340/242, 237 R; 73/40; 338/34; 200/61.03; 285/93

[56] References Cited

U.S. PATENT DOCUMENTS

| | | | |
|---|---|---|---|
| 1,271,865 | 7/1918 | Doods | 340/242 X |
| 1,281,329 | 10/1918 | Flannery et al. | 340/242 X |
| 2,306,509 | 12/1942 | Talmey | 200/61.03 |
| 3,407,123 | 10/1968 | Peterson | 73/40 X |
| 3,721,898 | 3/1973 | Dragoumis | 340/242 X |
| 3,721,970 | 3/1973 | Niemoth | 340/242 |
| 3,753,257 | 8/1973 | Arnold | 340/236 |
| 3,882,382 | 5/1975 | Johnson | 340/242 X |

FOREIGN PATENT DOCUMENTS

0110439 10/1917 United Kingdom ................ 340/237 R

*Primary Examiner*—Daniel M. Yasich
*Attorney, Agent, or Firm*—Townsend and Townsend

[57] ABSTRACT

An improved gas leakage indicating device of the type in which an electrical warning signal is generated. Electrically conductive material which is chemically reactive with the particular gas to be sensed comprises part of an electric circuit. The electrically conductive material is located proximate connections or seals in the gas vessels so that in the event of a leak the gas chemically reacts with the conductor. The subsequent destruction or degradation of the conductor breaks the electric circuit, thereby generating the appropriate warning signal.

4 Claims, 9 Drawing Figures

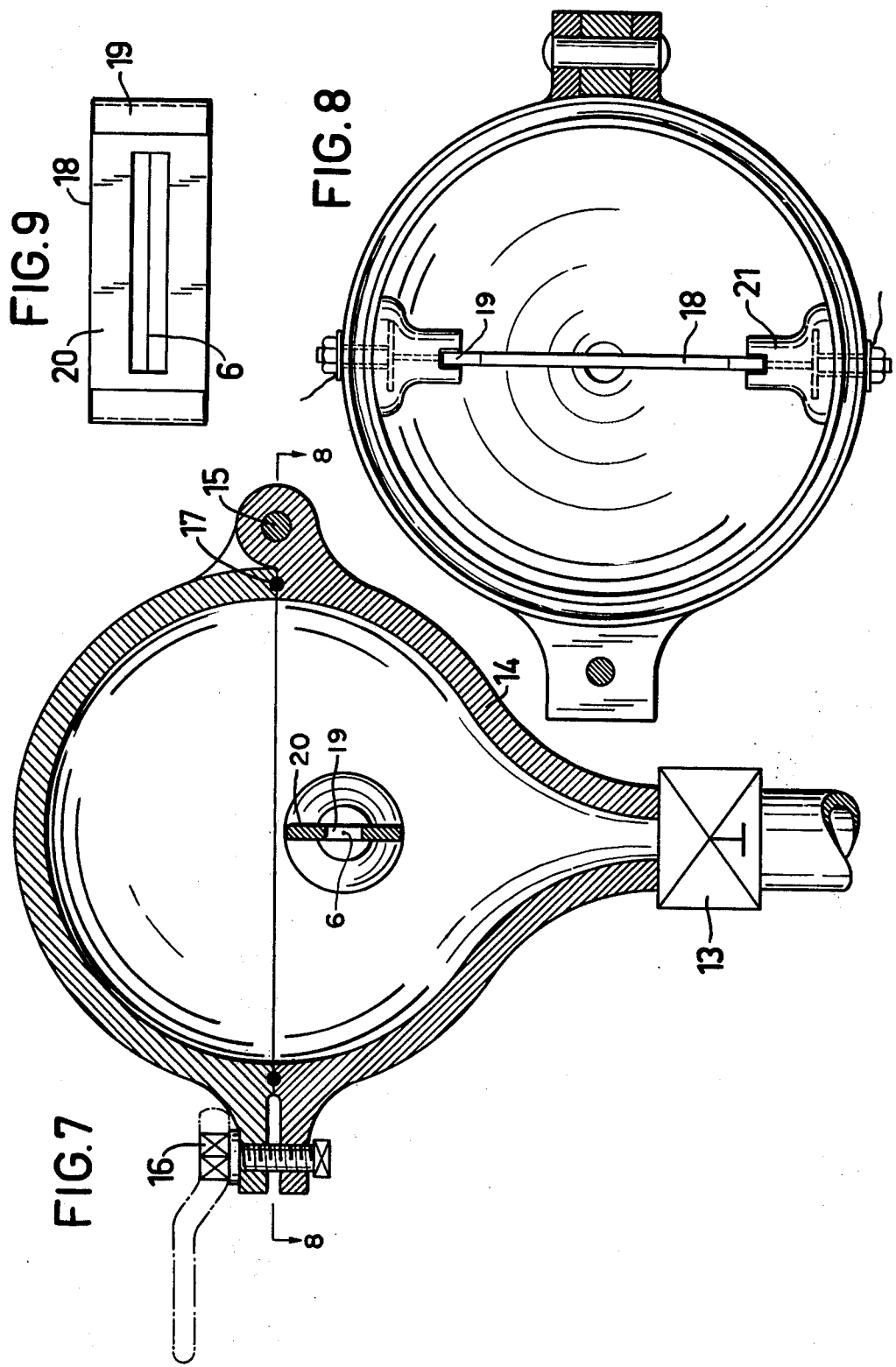

GAS LEAKAGE INDICATION DEVICE

In many industries poisonous liquids and gases must be used which often are to be transported over long distances in pipelines. Such piping unavoidably includes a number of weak points at joints, drain conduits and the like, and leakage can occur in spite of all precautionary measures.

Leakage of liquids generally can be detected easily, but leakage of gas of the type chlorine and several other does not cause perceptible indication, but the gas has the opportunity of rapid spreading. Chlorine is a highly poisonous gas to inhale and, therefore, constitutes great risk for a person entering such a gas-filled room or being exposed to the outflowing gas, which can spread to cover a whole community when the wind and other conditions promote such spread.

It is known to take measures at connections and similar suspicious places, for example by providing an ammonia wick in a plastic tube about these places. In the event of chlorine gas leakage, ammonium chloride develops and manifests itself in the form of a distinct white smoke signal, at the same time as the outflowing chlorine is neutralized during this first phase by the ammonia. The white smoke serves as an indicator and renders possible immediate repair measures.

Also indicators of other types are known, for example a dry wick, possibly impregnated with a suitable material, which in the case of leakage gets moist and assumes a higher conductivity, thereby causing an applied voltage to pass ahead a current, which in its turn indicates the existence of danger, usually by means of a relay, which switches-on a signal or the like. Several such electric resistances can be connected in series, but they do not indicate the place of the leakage but only the fact that leakage is going on.

Also gas detectors for other gases are known, for example a filter absorbing e.g. mercury vapour, which increases the electric conductivity of the filter. When a flow through the filter has obtained a certain value, an alarm is released.

There exist also special detectors and alarm devices, which generally are based on the principle that a certain amount of air is taken in by suction and combusted. The heat produced shows the presence of carbon monoxide. Also other carbon monoxide indicators are known, but they are expensive and scarcely suitable for use as signal transducers in the case of leakage.

The present invention relates to a detector installation for detecting leakages in piping of the aforedescribed kind. The detector installation according to the invention substantially is characterized thereby that at connections, drain cocks and similar places where leakage can be suspected to arise, one or more coils or wires are provided of a suitable material, which has such properties relative to the gas possibly leaking out, that the coil or strand is corroded or exposed to such chemical attacks (pitted), that it breaks. The coil, according to the invention, can either be held stretched by a spring or the like in a manner known, for example, from electric safety fuses, and where upon break of the material the spring is released which thereby indicates the presence of leaking gas. The wire or coil, according to the invention, can also be held at an electric voltage producing an electric quiescent current therethrough, which current is interrupted when the coil or wire breaks and thereby electrically releases a signal. According to a further embodiment of the invention, both a spring is used for ensuring the interruption, and an electric signal device is used for indicating where the break has occurred. In this lastmentioned case, the device according to the invention can be arranged so as to actuate signal lamps or the like at a common control pulpet or the like which permanently is observed.

The indicator installation according to the invention can be designed in many different ways, depending above all on the gas against which the device is intended to protect. In the following embodiments are described where the dangerous gas is chlorine gas and where wires or coils of zinc or some suitable alloy are used which rapidly are corroded when chlorine gas leaks out.

When poisonous gases other than chlorine are transported in the pipelines, it is important to find a suitable substance, which is corroded or pitted just by that gas. The mode of operation and design of the device, however, are in all these cases the same.

With reference to the accompanying drawings, embodiments of such chlorine gas warning devices are described in greater detail where zinc or zinc alloys are used as indicating and signal releasing means.

In the drawings,

FIG. 7 is a section through an indicator bell intended for connection, for example, to a cistern or the like in order to prevent the cistern from being opened through a manhole or the like when the container is filled with corrosive gas.

FIG. 8 is a section through the same device as in FIG. 7, seen in the direction of the arrows B—B.

FIG. 9 shows a side view of an inserted fuse element with a conductive wire sensitive to gas clamped in said element.

Figures 1, 2, 3, 4:
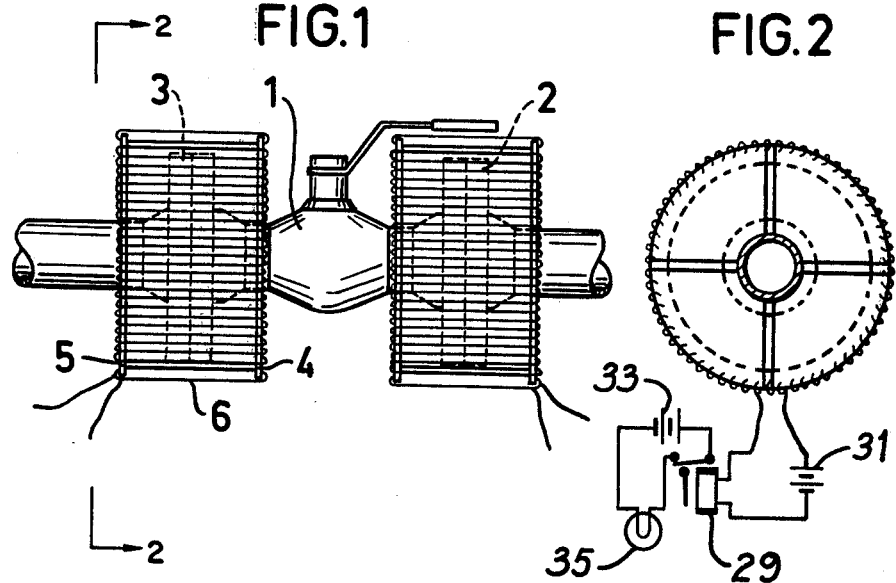
FIG. 1 shows two indicators according to the invention arranged each on one side of a valve, each enclosing a flange connection.
FIG. 2 shows the same device seen in the direction of the arrows A according to FIG. 1.
FIG. 3 shows a similar device at a pipe connection.
FIG. 4 shows the same device seen in the direction of the pipe.

The embodiment shown in the Figures is adapted to a piping for chlorine gas. As indicator is used a wire of zinc or some alloy, which easily is influenced (attacked) by the chlorine gas. In FIG. 1 is shown how a valve 1 is connected in a pipe conduit by means of flange connections 2 and 3. The flanges are enclosed by two discs 4 and 5, which at their edges are provided with grooves, into which a zinc wire or the like 6 has been inserted in a zigzag manner, so that a cage is formed about the flange. FIG. 2 shows the same device seen from the side and illustrates the closed electrical circuit through which current is flowing. For example, the closed electrical circuit may be the energizing circuit of a circuit closing relay 29. A battery 31 or other power source provides the quiescent current through the energizing circuit. The relay circuit includes a battery 33 and any type of indicator, such as lamp 35. Upon the corrosion of the conductor by the leaking gas, the quiescent current in the energizing circuit is interrupted and relay 29 is closed, thereby lighting lamp 35.

FIGS. 3 and 4 show a similar device attached about a welded pipe connection where two discs 4 and 5 enclose the connection and a zinc wire or the like is wound about in zigzag and inserted in grooves in the edges of the discs.

As soon as a leakage occurs, the zinc wire is corroded, and an applied quiescent current is interrupted which, for example via a relay, produces an indication on an alarm signal plate or the like.

Figure 5:
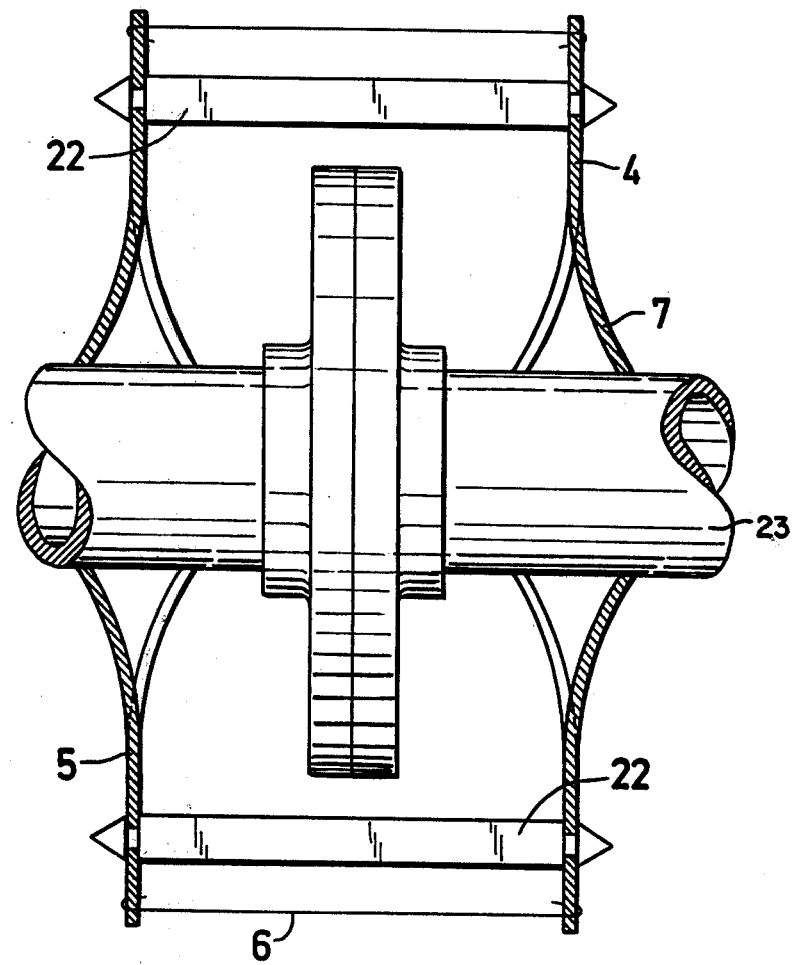
FIG. 5 shows on an enlarged scale a section through the same kind of indicator as in FIG. 1.
Figure 6:
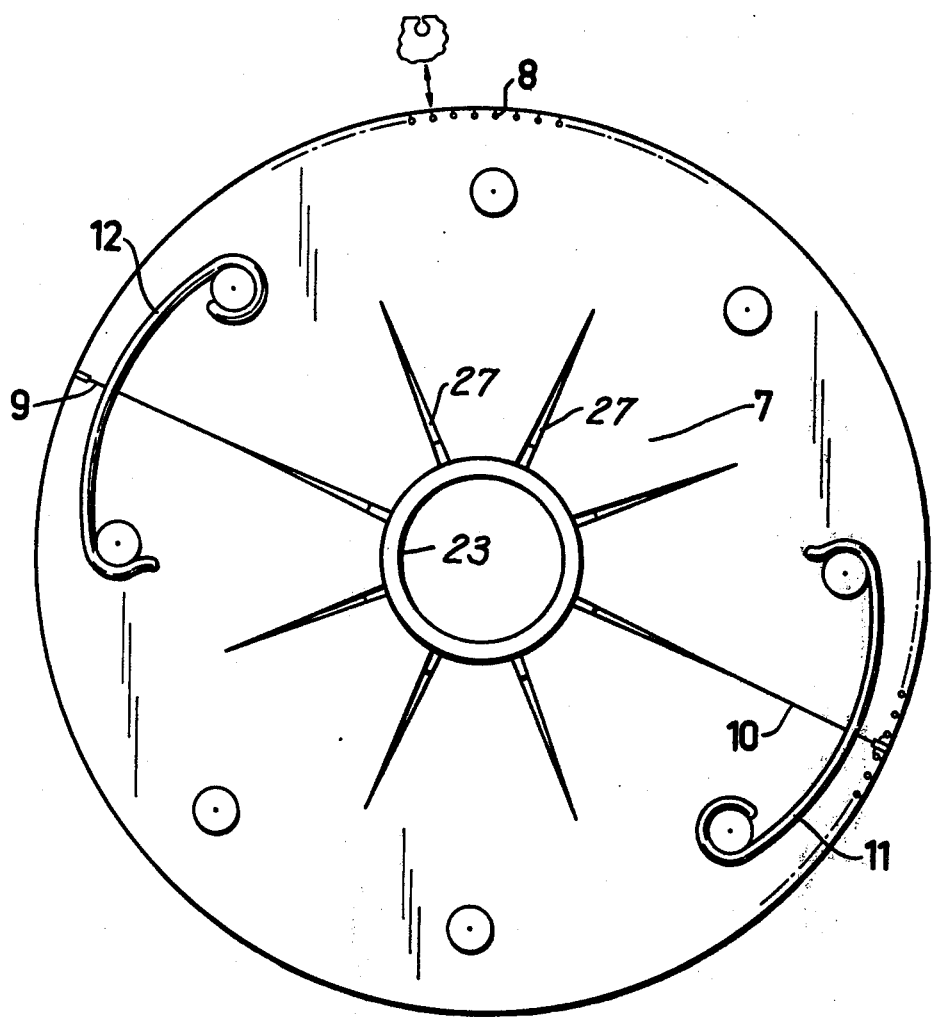
FIG. 6 shows the same device seen from the side.

Details of the invention depicted in FIGS. 1 through 4, including the disks 4 and 5 which direct the leaking gas toward the zinc wire 6, can be better understood by referring to FIGS. 5 and 6.

FIGS. 5 and 6 show on an enlarged scale in detail how a gas detector according to the invention is designed. The discs 4 and 5 are provided with tips 7 adapted to be bent laterally and providing support against the pipe 23. The discs 4 and 5 are held spaced from each other by spacing pins 22, and the zinc wire 6 or the like is wound reciprocally between the discs and inserted in grooves 8, one of which is shown in detail by way of a piece broken out uppermost in FIG. 6. The disks thus serve to contain the leaking gas and generally direct it radially outward from the pipe connection toward the zinc wire 6. In order to facilitate the mounting, the discs are at 9 and 10, respectively, divided into two halves, which are held together in mounted state by springs 11 and 12. Referring to FIGS. 5 and 6, each of the disk halves has radially directed slots 27 which define flexible ribs or tips 7. The tips 7 are flexible in an axial direction relative to one another so as to provide supporting legs to the pipe 23, as shown in FIG. 5. The combination of the springs 11 and 12 which secure the disk halves to one another and the flexible tips 7 on each of the disk halves permits the disks 4 and 5 to be releasably secured to pipe 23 and supported in a position generally perpendicular to the longitudinal direction of pipe 23. At the edges of the discs contact means are so provided, that at the mounting of the detector about the pipe the respective wire coils are conductively connected to each other.

FIG. 7 shows a meter bell intended to be connected to a manhole or the like in a cistern for chlorine gas, for example. The control device is connected via a valve 13 to the container or the like, and upon opening of said valve gas can flow into the meter bell 14. The bell is divided into two halves, which are hingedly connected to each other at 15 and held together by a lock 16 or the like on the opposite side. Said lock 16 can be designed as an electrically controlled magnet coupling, which upon its opening automatically closes the valve 13. A sealing ring 17 prevents leakage. In said bell, as appears from FIG. 8, an indicator 18 is provided, which is shown seen from the side in FIG. 9.

The indicator consists of a metal wire 6 clamped between two bars 19 of stainless steel or the like. Said stainless bars are held spaced by a perforated plastic membrane 20 or the like. This unit is inserted between two insulated holders 21 in the casing, and through said insulating material extend two lines permitting a current be passed through the wire. When a test is to be made whether a blown tank can be opened, the valve 13 is opened for a certain time. When the wire thereby is corroded, the current is broken, and the magnet lock 16 is locked so that it cannot be opened unless the valve 13 has been closed, and then the bell can be opened for wire exchange.

The aforedescribed embodiments, thus, are based thereon that a conductive wire in principle is corroded and thereby causes current interruption. Said interruption, in the case described, gives rise to an impulse to a central installation, which notes the interruption of the control current. It can be suitable in many cases to provide each detector in a separate current coil, which in a simple manner shows which flange connection or the like is leaky. It also is possible to arrange the detectors in series and to supply them with pulses in such a manner, that upon the breaking of a pulse a central installation can identify the detector, which has been subjected to current interruption.

For other gases reactants other than zinc wire can be required. If a material can be found which is influenced in the same manner, i.e., attacked chemically, devices according to the invention can be used also in these cases. As this material possibly may not be attacked as rapidly as the zinc is attacked by chlorine, it may be suitable to attach a spring, which holds the meter wire stretched and causes it to break when the wire has become sufficiently thin.

The principle can be the same as at usual fuse plugs, for example, where as known a spring is provided to pull off the wire and to lower a signal to show which plug has blown. The difference, thus, is that the wire in the present case is exposed to the corrosive gas.

It can be mentioned in this connection that it may be suitable to enclose the zinc wire or the like in a tube of perforated plastic or the like in order to prevent the wire from contacting conductively the material in the piping or the like. It is, of course, also possible to provide the wire, for example, with a tape as carrier, in which case the tape brings about the insulating abutment on one side, while the outwardly facing end of the wire is exposed to the corrosive gas.

The device according to the invention, of course, can be varied in many different ways. It can also be designed as a manual instrument where an easily exchangeable active wire is retained between, for example, two resilient arms and is moved about suspected places. As soon as the wire is attacked and broken, the resilience is released and indicates visibly that a leakage exists. In this case where an active wire or the like is loaded by a spring, it can be used for the release of a signal, as above. No electric current must be applied, and the device, therefore, is more handy and cheaper. Mechanic signals for being reliable require permanent observation.

What I claim is:

1. In an electrically-operated gas leakage indicating system for detecting the leakage of gas from a tubular vessel and utilizing a closed electrical circuit through which current is flowing, a gas leakage sensing apparatus which comprises:

first and second disks protruding radially from the tubular vessel and spaced apart from one another so as to straddle a location on the vessel at which gas leakage is to be detected, each of said disks having a generally annular shape, a central opening for fitting over the tubular vessel, and a plurality of radially-directed selectively bendable tips extending generally to the perimeter of said central opening for supporting said disk generally perpendicular to the tubular vessel; and at least one electrical conductor forming a portion of the closed electrical circuit and constructed of material which is chemically reactive with the gas, said conductor being secured to said spaced-apart disks radially outward of the tubular vessel, whereby leaking gas is directed by said disks radially outward toward said conductor so as to interrupt the electric current passing through said conductor.

2. Apparatus according to claim 1 wherein each of said disks further comprises a pair of disk segments, each of said disk segments having a generally semi-circular cutout for fitting over the tubular vessel; and including means for securing said disk segments to one another so as to form a substantially continuous annular disk.

3. Apparatus according to claim 1 wherein said conductor comprises a multiplicity of interconneced wires, said wires extending between said spaced-apart disks generally parallel to the tubular vessel and being substantially equally distributed around said disk so as to surround the tubular vessel.

4. In an electrically-operated gas leakage indicating system for detecting the leakage of gas from a tubular vessel and utilizing a closed electrical circuit through which current is flowing, a gas leakage sensing apparatus which comprises:

first and second disks protruding radially from the tubular vessel and spaced apart from one another so as to straddle a location on the vessel at which gas leakage is to be detected, each of said disks further comprising a pair of disk segments, each of said disk segments having a generally semi-circular cutout for fitting over the tubular vessel and a plurality of radially inward directed flexible tips, and means for securing said disk segments to one another so as to form one of said disks, whereby said tips are flexed in an axial direction relative to one another so as to support said disks in a position generally perpendicular to the tubular vessel when said disk segments are secured to one another by said securing means; and at least one electrically-conductive wire forming a portion of the closed electrical circuit and constructed of material which is chemically reactive with the gas, said wire interconnecting said spaced-apart disks at a plurality of points around said disks so as to generally surround the vessel proximate the location where gas leakage is to be detected, whereby leaking gas is directed by said spaced apart disks radially outward from the tubular vessel toward said wire so as to interrupt the electric current passing through said wire.

* * * * *